United States Patent
Fischer et al.

(10) Patent No.: US 8,915,913 B2
(45) Date of Patent: Dec. 23, 2014

(54) ELECTROSURGICAL INSTRUMENT

(75) Inventors: Klaus Fischer, Nagold (DE); Daniel Schäller, Tübingen (DE); Achim Brodbeck, Metzingen (DE); Markus Enderle, Tübingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 489 days.

(21) Appl. No.: 13/390,135

(22) PCT Filed: Jul. 21, 2010

(86) PCT No.: PCT/EP2010/004470
§ 371 (c)(1),
(2), (4) Date: Feb. 13, 2012

(87) PCT Pub. No.: WO2011/018153
PCT Pub. Date: Feb. 17, 2011

(65) Prior Publication Data
US 2012/0150167 A1    Jun. 14, 2012

(30) Foreign Application Priority Data

Aug. 14, 2009 (DE) .......................... 10 2009 037 613

(51) Int. Cl.
*A61B 18/18* (2006.01)
*A61B 18/14* (2006.01)
*A61B 18/00* (2006.01)

(52) U.S. Cl.
CPC ....... *A61B 18/1447* (2013.01); *A61B 2218/002* (2013.01); *A61B 2218/007* (2013.01); *A61B 2018/1475* (2013.01); *A61B 2018/0016* (2013.01)
USPC .................................. 606/51; 606/50; 606/49

(58) Field of Classification Search
CPC ................... A61B 18/1445; A61B 2018/0063; A61B 18/1442
See application file for complete search history.

(56) References Cited

U.S. PATENT DOCUMENTS 5,222,973 A   6/1993  Sharpe et al.
6,273,887 B1  8/2001  Yamauchi et al.

FOREIGN PATENT DOCUMENTS

| DE | 600 17 272 T2 | 12/2005 |
|---|---|---|
| DE | 699 35 139 T2 | 10/2007 |
| EP | 1 151 723 A2 | 11/2001 |
| EP | 1 878 400 A1 | 1/2008 |

*Primary Examiner* — Christopher D Koharski
*Assistant Examiner* — Philip Edwards
(74) *Attorney, Agent, or Firm* — Dickstein Shapiro LLP (57) ABSTRACT

An electrosurgical instrument for minimally invasive surgery, the instrument including two gripping parts which can be brought together into a gripping direction or moved apart counter to the gripping direction. At least one gripping part includes three or more electrically conductive sections, electrically insulated relative to each other. Each electrically conductive section may be separately connected to a high frequency (RF) current generator such that each electrically conductive section can be configured in various electrical configurations by the RF current generator.

16 Claims, 7 Drawing Sheets

ELECTROSURGICAL INSTRUMENT

CROSS REFERENCE TO RELATED APPLICATIONS

This application is the U.S. national stage of claims priority to PCT/EP2010/004470, filed Jul. 21, 2010 and published as WO 2011/018153, which claims priority to DE102009037613.5, filed Aug. 14, 2009.

FIELD OF THE DISCLOSED EMBODIMENTS

The disclosed embodiments relate to surgical instruments, and more particularly to electrosurgical pincettes or forceps, for minimally invasive surgery.

BACKGROUND OF THE DISCLOSED EMBODIMENTS

European Patent EP 1 151 723 B1, by the Applicant, discloses a surgical instrument that includes two gripping parts that can be brought together in a gripping direction or moved apart counter to the gripping direction. Each of the gripping parts has a first inner and a second outer limb with a bending region, the limbs being at a distance from each other in the gripping direction. The surgical instrument's inner limbs of the gripping parts are arranged inside a guide sleeve and can be moved in the longitudinal direction of the guide sleeve relative to the outer limbs of the gripping parts in such a manner that, with a movement of the limbs relative to each other in their longitudinal direction, the respective gripping part can be moved in the gripping or counter-gripping direction. One limb of the first gripping part can be connected to a first connector of an RF (high frequency) current generator and the inner limb of the second gripping part can be connected to a second connector of the RF generator, and the limbs are electrically insulated from each other.

Such surgical instruments are used in minimally invasive surgery, for example, for grasping tissue, small vessels or similar such materials. Like forceps or pincettes, such an instrument includes movable gripping parts that can be brought together or moved apart for gripping in a gripping direction or a counter gripping direction. Due to their small dimensions, the instruments can preferably be used in the working channel of an endoscope.

The instrument in accordance with EP 1 151 723 B1 has proven itself in clinical applications. However, the need for further improvement has arisen. Therefore, it is the object of the disclosed embodiments to provide an improved electrosurgical instrument that offers further increased efficacy and safety when handled in practical applications.

BRIEF SUMMARY OF THE DISCLOSED EMBODIMENTS

The disclosed embodiments improve the working options of the physician by dividing at least one of the two gripping parts of the instrument into functionally different sections. For this purpose, the first and/or the second gripping part have several conductive sections extending in the longitudinal direction of the instrument, each of these sections being associated with a pair of inner and outer limbs. In one embodiment, the individual pairs of inner and outer limbs may be electrically insulated from each other and may be connected separately to an RF current generator. Referring to this embodiment and considering different modifications of the connection of the limbs (and thus the associated sections of the respective gripping part), it is possible to implement different field configurations in the distal effective region of the instrument with the use of an RF current generator.

In one embodiment, each of the first and/or second gripping parts has three or more insulated conductive sections and pairs of inner and outer limbs. In particular, it is possible to provide exactly three conductive sections and pairs of limbs in order to produce different configurations of the electrical field between the gripping parts.

Another embodiment provides that the distance between the inner and the outer limbs of the associated pair of limbs of a gripping part divided into sections be greater than the distance of the limbs associated therewith. As a result of this, the circular or elliptical cross-section of the guide sleeve of the limbs can be optimally used in a statically advantageous manner, and an instrument exhibiting strong gripping forces and low-loss force transmission can be implemented.

Another embodiment provides that the surface of the first and/or second gripping part respectively facing the other gripping part be inclined or curved, at least in sections, in such a manner that, in a brought-together state, a gap of longitudinally uneven width is formed between the gripping parts. The result of the application of a voltage to the first and the second gripping parts with such a gap results in a linearly or non-linearly varying electrical field strength of the electrical field formed between the first and the second gripping parts in the longitudinal direction. This, too, increases the working options with the suggested instrument on the part of the physician in coping with different clinical situations.

Another embodiment provides that at least one of the sections of a gripping part be movably supported in the gripping part or opposite thereof. In particular, the configuration is such that a section with an inclined or curved surface is movably supported in the respective gripping part in such a manner that it can be moved separately toward or away from the other gripping part. This, among other things, makes possible a certain uncoupling between the mechanical and electrothermal (coagulating) functions of the instrument.

Another embodiment provides that the movably supported section having a curved surface be accommodated in the respective gripping part in such a manner that the gripping part performs a rolling-off movement relative to an opposite surface of the other gripping part when the instrument is moving towards a brought together state. In doing so, in the process of closing the instrument, the point of the smallest distance between the opposing gripping part surfaces moves in the direction of the distal end of the instrument. Each of the first and the second gripping parts has three insulated sections with one associate pair of inner and outer limbs, and the respective movably supported sections have an inclined or curved surface.

Another disclosed embodiment provides that the movable section be guided within the gripping part in the gripping direction, in particular by an adjacent stationary section of the same gripping part. As a result of this, it is possible to perform precisely controlled mechanical functions such as, for example, a mechanical severing operation.

Another embodiment of the instrument includes a guide for laterally guiding the first and the second gripping part. The guide is active, at least in the mostly closed part of the instrument. The guide for lateral guidance may be provided on one or more of the plurality of insulated sections of the one or more gripping parts that are divided into sections. As a result, it is possible to largely preclude potential jamming of the gripping parts or of the sections thereof relative to each other, as well as unintentional contusing of tissue grasped with the instrument.

Another embodiment provides that at least one insulating section acts as a spacer between two insulated conductive sections for the adjustment of a prespecified minimum distance between the opposing conductive sections in a brought-together state of the instrument. Consequently, it is possible to prevent short circuits when the instrument is handled, such short circuits otherwise occurring when a vessel or other tissue fails to be grasped and the conductive gripping parts or sections thereof can come into direct contact with each other.

DETAILED DESCRIPTION OF THE INVENTION

In the description hereinafter, the same reference signs are used for the same parts and for parts having the same function.

Figures 1, 2:
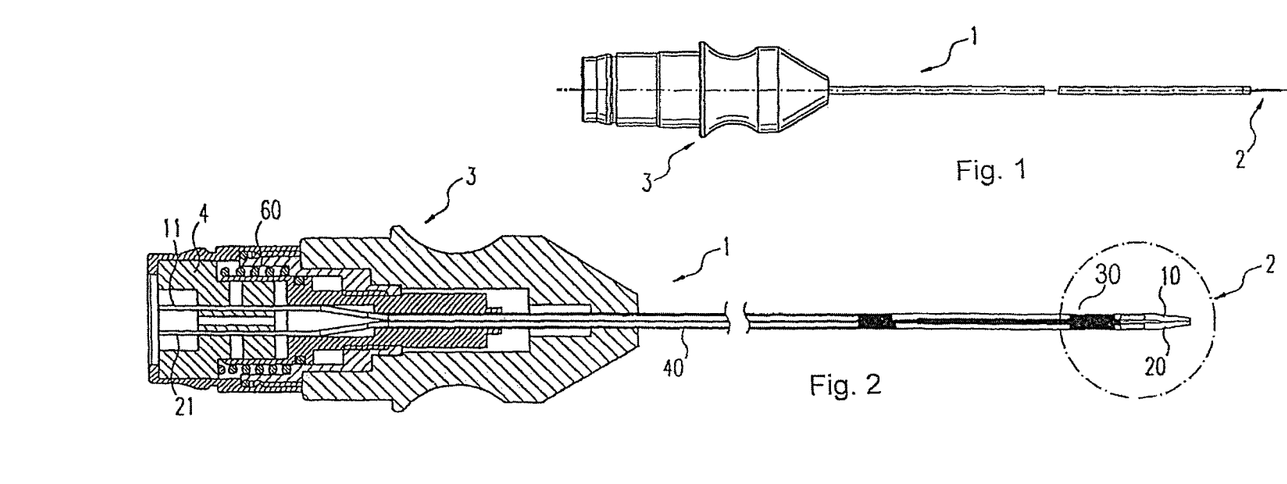
FIG. 1 is a longitudinal sectional view of a surgical instrument.
FIG. 2 is a longitudinal sectional view of a surgical instrument.

FIG. 1 shows a complete side view of the surgical instrument 1 with the instrument tip 2 and a manipulative handle 3. FIG. 2 shows a longitudinal sectional view of the surgical instrument shown by FIG. 1.

Referring to, FIG. 2, the design of the manipulative handle 3 and, in particular, its mode of function is particularly well recognizable. First limbs 11 and 21, extend from a first and a second gripping part 10 and 20, respectively, through a guide sleeve 30 and a tube 40 up to an actuating device 4 that is supported in the manipulative handle 3 and is disposed for bringing the gripping parts 10 and 20 together in a gripping direction or apart counter to the gripping direction. A helical spring 60 is used to push the actuation device 4 out of the handle 3 against an abutment, whereupon a pulling force in the longitudinal direction of the tube 40 and the guide sleeve 30 is exerted on the first limbs 11 and 21 of the gripping parts 10 and 20, so that the gripping parts 10 and 20 are brought together. This corresponds to the inoperative position of the instrument 1.

By applying pressure on the actuation device 4 or by pushing the actuation device 4 into the manipulative handle 3 while the helical spring 60 is being compressed, a pushing force is exerted on the first limbs 11 and 21. The pushing force can move the first limbs 11 and 21 away from the manipulative handle 3 in the longitudinal direction of the tube 40 and the guide sleeve 30. This causes a torque at the instrument tip 2 around the mounts of the second limbs 12 and 22 (FIGS. 3A-3C) on the guide sleeve. The torque causes the gripping parts 10 and 20 projecting from the guide sleeve 30 at the instrument tip in the bending regions 13, 14 and 23, 24 (FIGS. 3A-3C) to bend outward, thus causing the gripping parts 10 and 20 to move apart counter to the gripping direction.

A tissue may be enclosed by the two gripping parts 10 and 20 and be grasped by removing the pressure from the actuation device 4. Without any manipulative pressure, the helical spring 60 again pushes the actuation device 4 out of the manipulative handle 3 thus applying a pulling force on the first limbs 11 and 21. The pulling force brings together the gripping parts 10 and 20 in the gripping direction and enables a grasping or gripping of the tissue. In doing so, the tissue is clamped between the two gripping surfaces of the gripping parts. Then, when the bending regions (13, 14, 23, and 24) have been pre-bent in the opening direction (see FIG. 7), with appropriate dimensioning of the helical spring 60, the entire system can be held together only due to the thusly occurring preliminary tension, i.e., also without any adhesion.

Figure 3A:
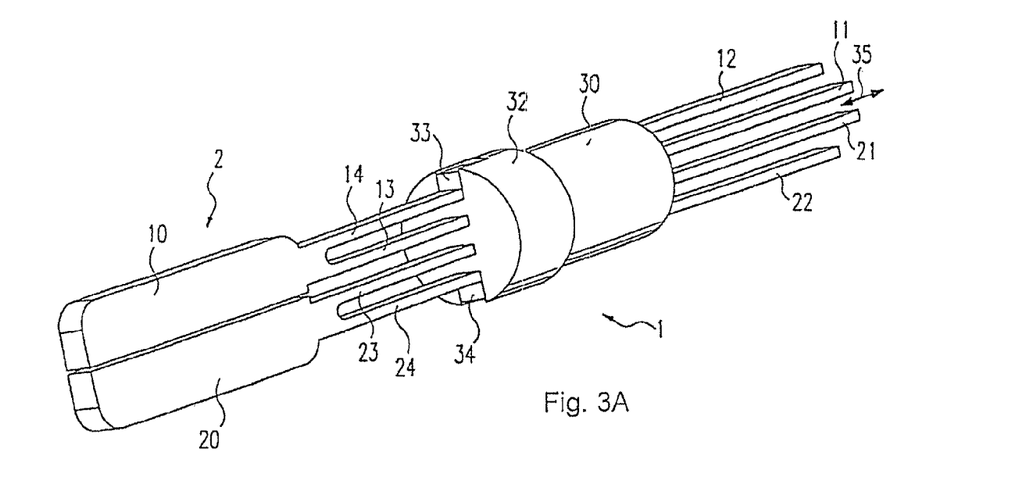
FIGS. 3A-3C are perspective and sectional views of the interior construction of the front part (distal part) of the surgical instrument of FIGS. 1 and 2, with FIGS. 3A and 3B showing the instrument in a brought-together state, and FIG. 3C showing the instrument in a moved-apart state.

FIG. 3A is a perspective view of a disclosed embodiment with the gripping parts brought together. FIG. 3A is different from FIGS. 1 and 2 in that the two gripping parts 10 and 20, the guide sleeve 30, and its cap section 32 are shown. In addition, the grasping surfaces of the two gripping parts 10 and 20 are smooth, i.e., they are shown without profile.

The first inner limbs 11 and 21, as well as the second outer limbs 12 and 22, of the gripping parts 10 and 20 are completely arranged inside the guide sleeve, essentially preventing any soiling or contamination and ensuring precise guidance. However, because it cannot be precluded that contaminants such as fluids, blood or similar substances enter into the instrument due to capillary action, the instrument is provided with a rinsing channel (not shown) for the purpose of cleaning.

The second limbs 12 and 22 have projections 33 and 34, respectively, that prevent a movement of the second limbs 12 and 22 in the longitudinal direction into the guide sleeve. The projections 33 and 34 are arranged in recesses of the cap section 32 that are provided for this purpose so that, in addition, a relative rotation of the gripping parts 10 and 20 into the guide sleeve 30 is prevented. Furthermore, the projections are disposed to fix the second limbs 12 and 22 in position on the guide sleeve 30. To accomplish this, it is possible to glue the projections 33 and 34, for example to the guide sleeve 30 and/or the cover cap 32, or to clamp the projections in the recesses of the cover caps 32.

Figure 3B:
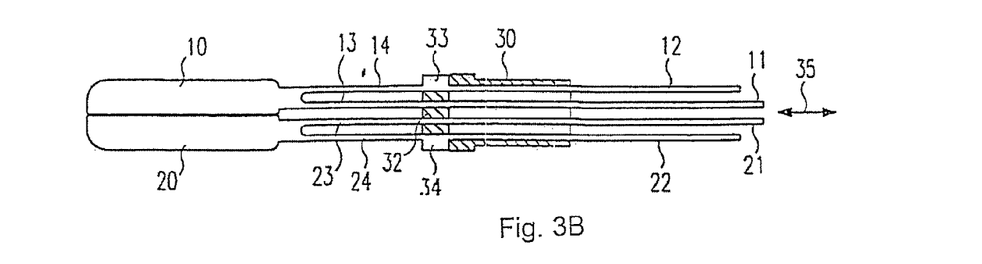
Figure 5A:
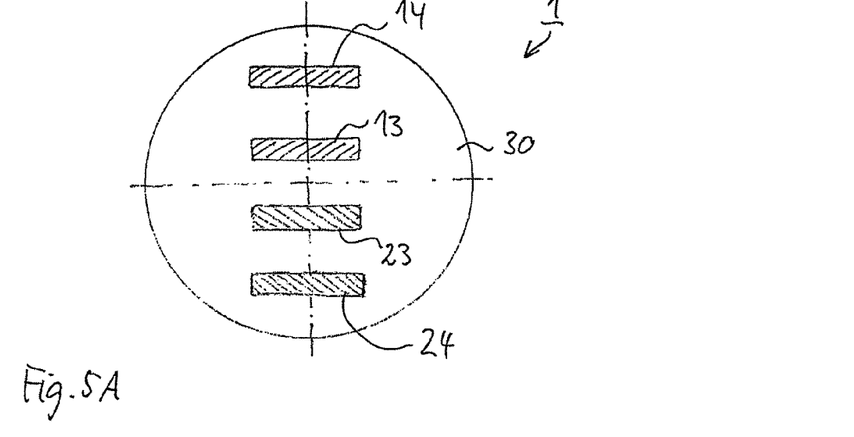
FIGS. 5A to 5C are schematic cross-sectional views showing and instrument in accordance with a disclosed embodiment looking in the longitudinal direction.

FIG. 3B shows a partial sectional view of an embodiment shown by FIG. 5A. The guide sleeve 30 consists of an insulating material, for example a plastic material. The first inner limbs 11 and 21 of the two gripping parts 10 and 20 have a design that is longer than that of the second outer limbs 12 and 22. The projections 33 and 34 of the second limbs 12 and 22, respectively, abut against the guide sleeve 30, such that they cannot be moved into the guide sleeve.

In order to move the gripping parts 10 and 20 apart or together, the longer first limbs 11 and 21 are moved in the longitudinal direction of movement indicated by the double arrow 35.

Figure 3C:
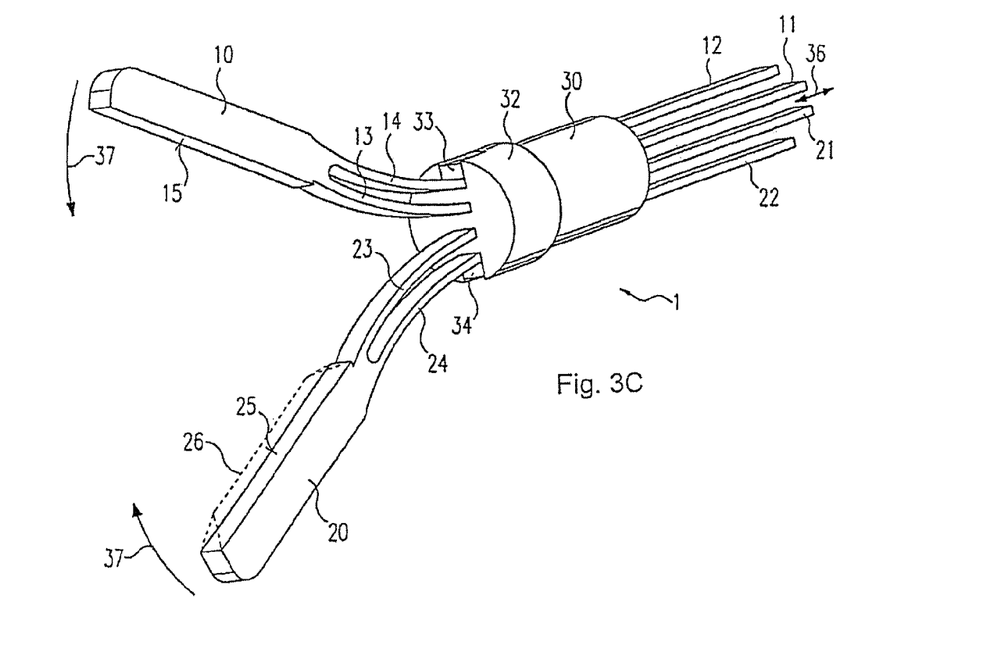

FIG. 3C shows an embodiment of the instrument with the gripping parts moved apart, in which case the limbs 13, 14, 23, 24 are pre-bent in the opening direction of the gripping parts 10, 20. Thus, in the inoperative position, the gripping parts of the instrument are moved apart. When the two inner or first limbs 11 and 21 are moved in the longitudinal direction away from gripping parts 10 and 20, gripping parts 10 and 20 are brought together. The movement causes a torque about the affixed two limbs 12 and 22, respectively, as a result of which the gripping parts 10 and 20 are bent in the bending regions 13 and 14 or 23 and 24 of the limbs 11 and 12 or 21 and 22, so that the gripping parts 10 and 20 are brought together in the gripping direction 37. The gripping surfaces 15 and 25 of the first and second gripping parts 10 and 20, respectively, can be seen well. At least one of the two gripping surfaces 15 or 25 may be configured as a cutting edge, the instrument 1 can also be used for cutting tissue or as a scissors. FIG. 3C shows an embodiment of profiled gripping surfaces 26 indicated in dashed lines.

Figure 4:
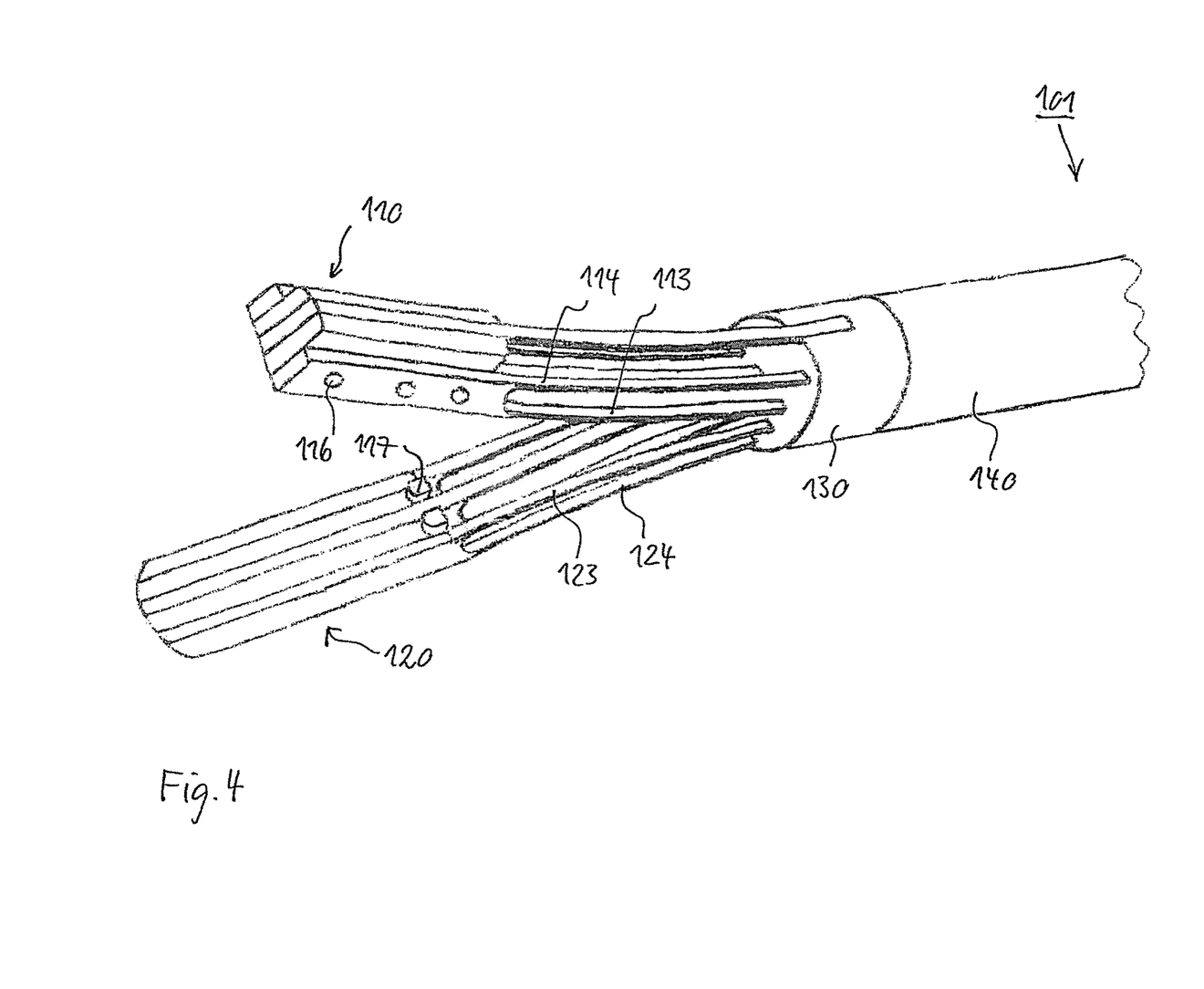
FIG. 4 is a perspective illustration of an instrument in accordance with a disclosed embodiment.

FIG. 4 is a perspective illustration of the distal end of an electrosurgical instrument 101. The instrument includes a guide sleeve 130 that is mostly inserted in a tube 140 and includes two limb arrangements projecting from the guide sleeve, each of the limb arrangements terminating in gripping parts 110 and 120, respectively, the gripping parts representing the distal end of the instrument 101.

Each gripping part 110, 120 is an assembly of a total of five individual (not individually identified here) material blocks that are connected to each other by means of screws 116. The outer elements and the center element are made of conductive material, and each includes associate inner and outer limbs. For the sake of greater clarity, FIG. 4 identifies these limbs only for one of the outer elements, i.e., with reference numbers 113 (inner limb) and 114 (outer limb) on the first gripping part 110 and with reference numbers 123 (inner limb) and 124 (outer limb) on the second gripping part 120.

The two blocks located between the outer elements and the center element of the gripping parts 110, 120 may comprise insulating material and may not have any associate limbs. A spacer block 117 is provided on each of the insulating interlayers in order to keep the metallic components of the gripping parts 110, 120 at a prespecified distance from each other, even if there is no vessel or tissue between the gripping parts, in order to avoid a short circuit when the RF voltage is switched on and the instrument 101 is in a brought-together state. The mode of movement of the instrument during the closing and opening process corresponds to the mode of operation of the instrument shown by FIGS. 1 to 3C, the instrument having been described farther above.

Figure 5B:
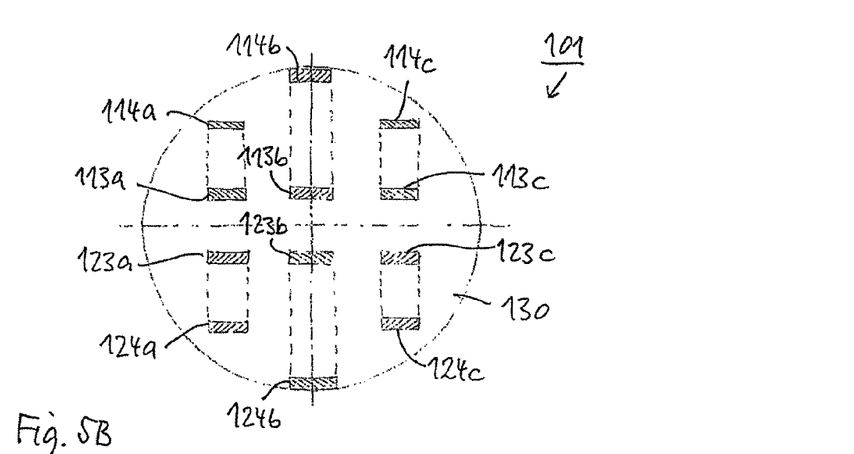
Figure 5C:
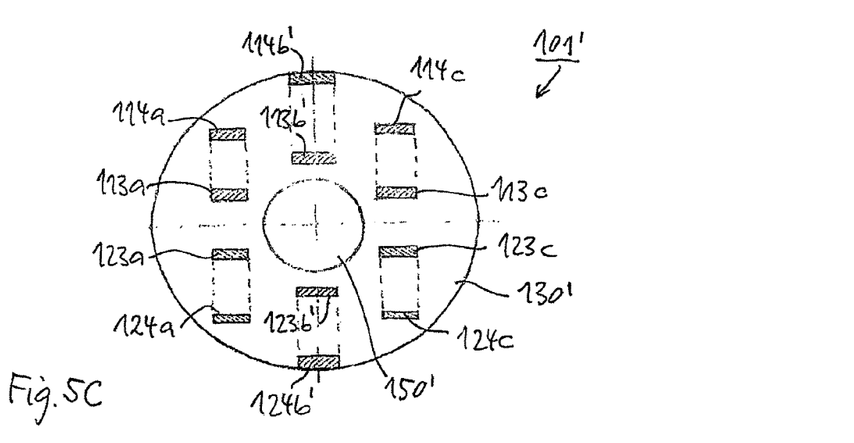
Figure 6A:
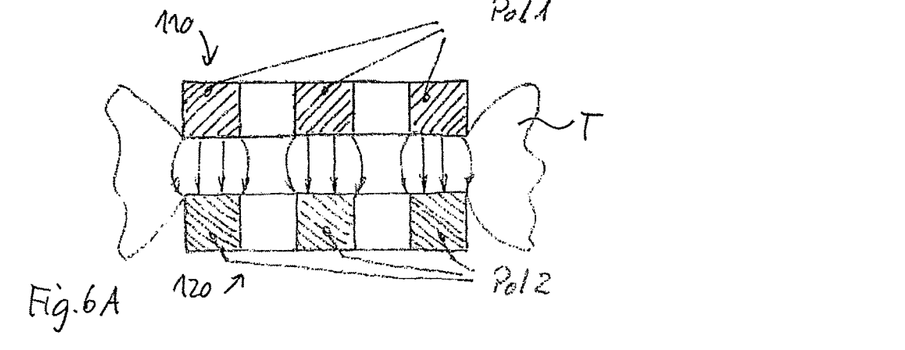
FIGS. 6A to 6D are schematic diagrams showing various electrical field configurations of an electrosurgical instrument in accordance with a disclosed embodiment.
Figure 6B:
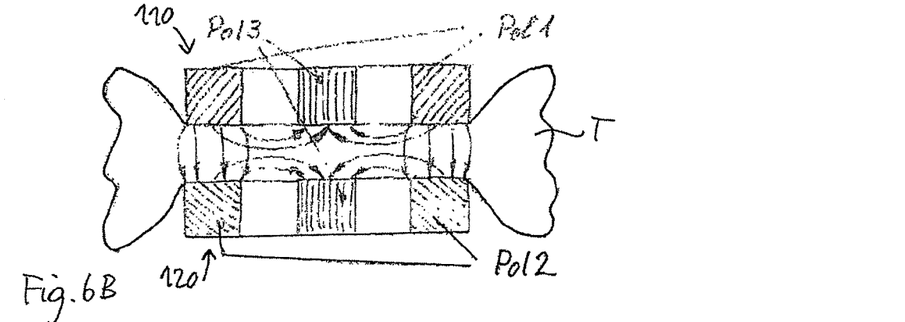
Figure 6C:
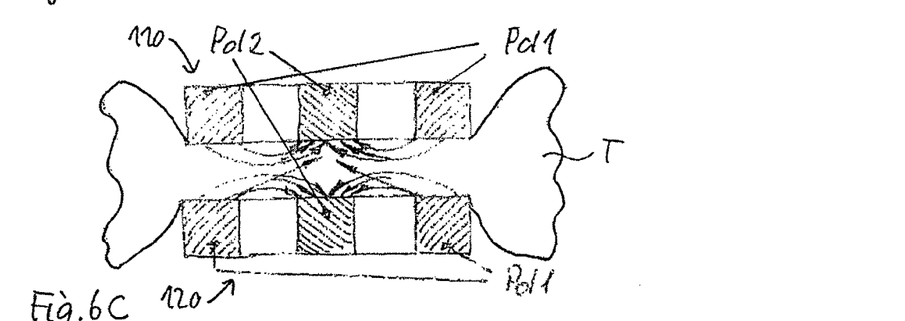
Figure 6D:
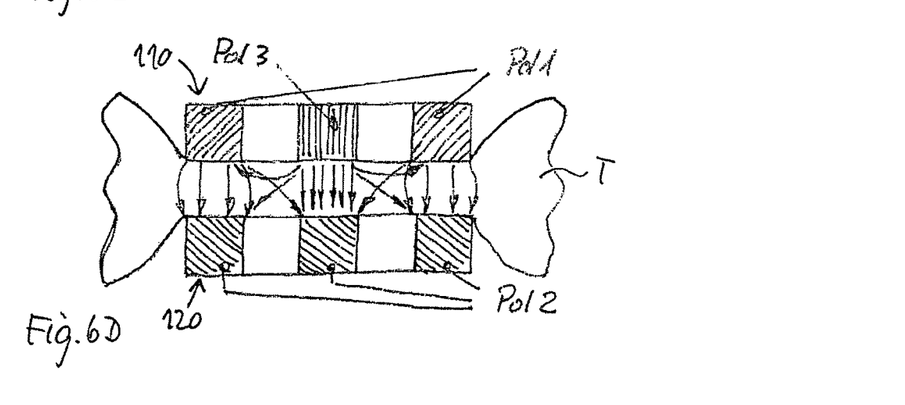

FIGS. 5A to 5C illustrate an aspect of the disclosed embodiments in that FIG. 5A shows a cross-section of the limb design of the instrument in FIG. 3 and FIG. 5B and 5C show a limb design of the instrument 101 and 101', respectively. Whereas, in the instrument 1 in FIG. 5A, each gripping part (not shown) is assigned only one single inner or outer limb 13, 23 or 14, 24, each of the instruments 101 and 101' includes three pairs of limbs, respectively, i.e., 113a/114a, 113b/114b, 113c/114c or 123a/124a, 123b/124b and 123c/124c. The instrument 101' as in FIG. 5C is similarly constructed; however, in the center of the guide sleeve 130' a rinsing channel 150' is provided, and the arrangement of the limbs 113', 114' or 123b', 124b' associated with the center element of the lateral gripping parts is slightly modified in order to create space for this rinsing channel 150'. The rinsing channel 150' can be used as a suction channel for evacuating fluids that must be removed from the treatment region or also as a rinsing channel for supplying fluid to the treatment region. The channel may also be used for removing or supplying a gas, or also for inserting an additional instrument.

FIGS. 6A to 6D show schematic cross-sectional views of the gripping elements 110 and 120. The elements are grasping a biological tissue T, and various circuitry configurations of each of the electrically conductive gripping element components (not separately marked), i.e., the connection to three poles, pole 1, pole 2, and pole 3 of an RF current supply are shown. Each of FIGS. 6A to 6D shows the configuration of the lines of electric flux passing through the tissue T and, therein, trigger various electrothermal and electrochemical effects, depending on the specific configuration of the lines of electric flux. These effects are not discussed in detail here as the embodiment shows that the division of the gripping elements into respectively three conductive components allows a plurality of such configurations.

FIGS. 7A to 7D are side views of the distal end of a first instrument (FIG. 7A) and a second instrument (FIGS. 7B to 7D), showing the operation of disclosed embodiments. Whereas, in the case of the instrument 101 as in FIG. 7A, the side surfaces of the first and the second gripping parts 110, 120 extend parallel to each other in a brought-together state, the corresponding surfaces 110a' or 120a' of the first gripping part 110' and the second gripping part 120' of a modified instrument 101' are curved.

Figure 7A:
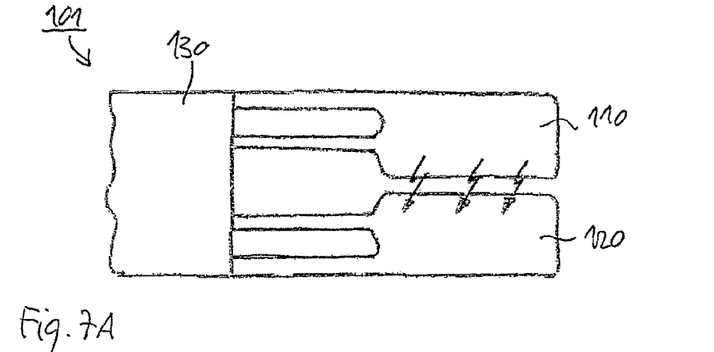
FIGS. 7A to 7D are schematic side views showing various opening and closing states of an instrument in accordance with a disclosed embodiment.
Figure 7B:
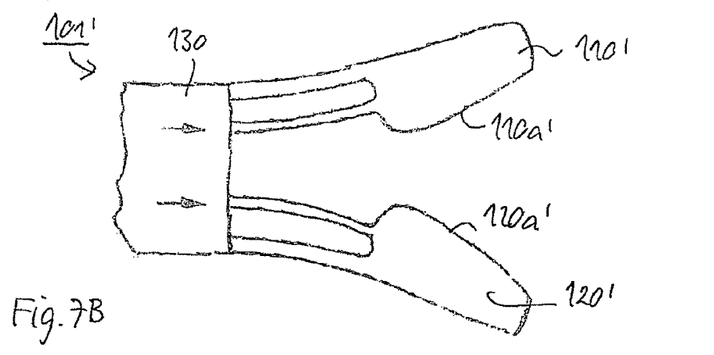
Figure 7C:
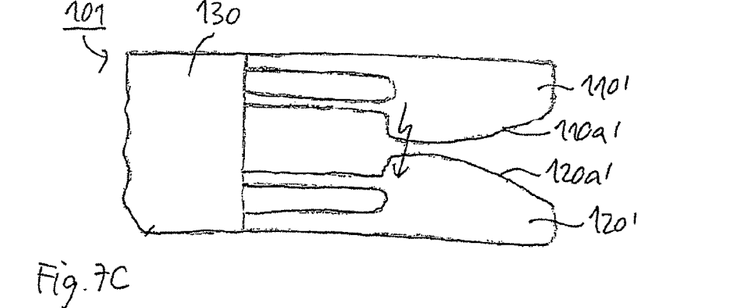
Figure 7D:
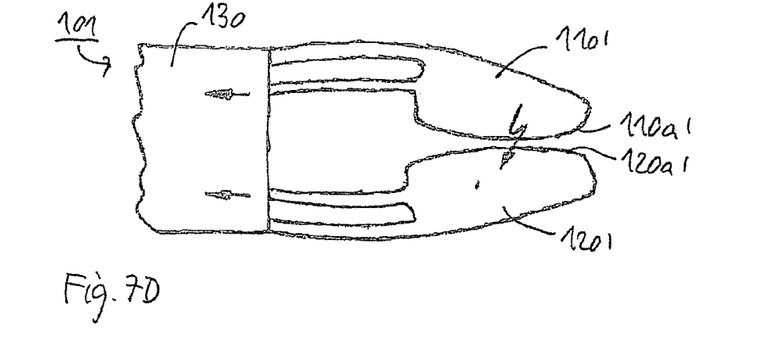

The (not illustrated) actuation mechanism acts in a manner such that, with the progressive closing of the instrument in the sequence shown in FIGS. 7B to 7D, a rolling-off movement takes place between the surfaces 110a', 120a' of the gripping parts 110' and 120', the surfaces facing each other. In the course of this movement, as symbolized by the location of the jagged arrow in FIGS. 7C and 7D, the point of the greatest electrical field strength migrates from the proximal end of the gripping parts in the direction of their distal ends. This can offer advantageous options for surgical use, e.g., the use of the instrument for a cutting operation in the manner of the action of a mechanical scissors. This is important for the movement shown in FIGS. 7B to 7D that a pushing force, as well as a pulling force, can be applied to at least the inner limbs.

Figure 8:
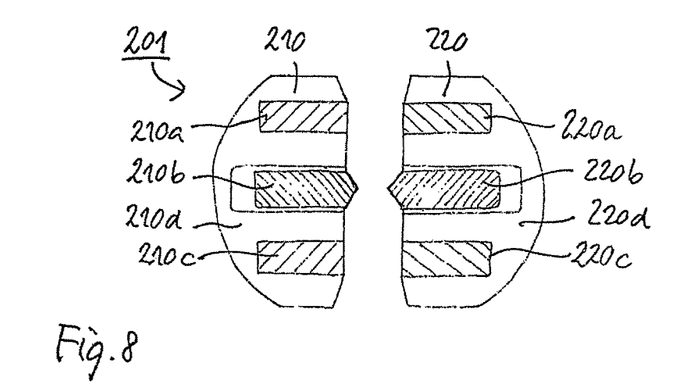
FIG. 8 is a schematic cross-sectional view of the distal end of an instrument looking in the longitudinal direction in accordance with a disclosed embodiment.

FIG. 8 is a schematic cross-sectional view of the distal end of an instrument 201. In a first gripping part 210, as well as in a second gripping part 220, two stationary outer metal parts 210a, 210c or 220a, 220c each are firmly embedded in a carrier body 210d or 220d, whereas a center element 210b or 220b is separately supported in a movable manner in the carrier body. The carrier body 210d or 220d may be an insulating material such as plastic. In addition, the opposing surfaces of the center elements 210b, 220b are provided with a cutting edge. Consequently, referring to the embodiment shown by FIGS. 7B to 7D and the embodiment described hereinabove, this embodiment makes possible a holding and cutting of vessels or biological tissue with a pulling force, as well as with a pressure force, that can be applied to the inner limbs.

Figure 9A:
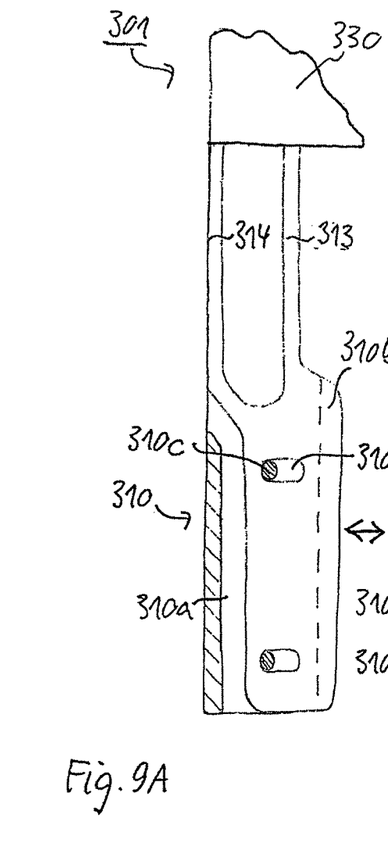
FIGS. 9A and 9B are partial side views of an instrument in two different states in accordance with a disclosed embodiment.
Figure 9B:
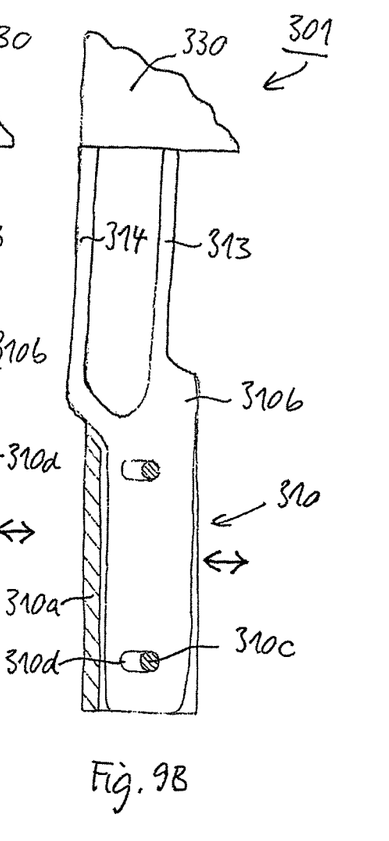

FIGS. 9A and 9B show another embodiment detailing the two different states of movement of only one of the two gripping parts of an instrument 301. The gripping part 310 includes a stationary part 310a and at least one movable part 310b that is configured in one piece with an inner and an outer limb 313, 314, respectively, and can be moved relative to the stationary part 310a into a grasping or cutting direction indicated by a double arrow when pushing forces or pulling forces are applied to the inner 313 and/or outer 314 limbs. The stationary part 310a is provided with guide pins 310c, and the stationary part 310a is provided with corresponding elongated holes 310 for engagement and for the sliding guidance of the guide or slide pins 310c. As a result of this arrangement, it is possible to perform particularly precise severing operations with the use of the appropriately configured instrument.

The implementation of the disclosed embodiments is not restricted to the examples described above and the emphasized aspects, but is rather likewise possible in a plurality of modifications lying within the scope of expert procedure.

The invention claimed is:

1. An electrosurgical instrument, comprising:
   two gripping parts which can be brought together into a gripping direction or moved apart counter to the gripping direction,
   wherein each gripping part includes, one bending region including at least one first and second limbs, the at least one first and second limbs being spaced apart from each other in the gripping direction,
   wherein at least the first limbs of the gripping parts are arranged inside a guide sleeve and can be moved relative to the second limbs in a longitudinal direction of the guide sleeve such that, with relative movement of the first limbs in the longitudinal direction, the respective gripping parts are moved in the gripping direction,
   wherein the first limbs are electrically insulated from each other, and at least one gripping part comprises three or more electrically conductive sections, electrically insulated relative to each other, that extend in the longitudinal direction of the instrument, and each of the conductive sections is electrically connected to a pair of the at least one first and second limbs, respectively, and
   wherein each pair of first and second limbs is electrically insulated with respect to each other and can be separately connected to an RF current generator such that each electrically conductive section can be configured in various electrical configurations by the RF current generator.

2. The electrosurgical instrument of claim 1, wherein the electrosurgical instrument is an electrosurgical instrument for minimally invasive surgery.

3. The electrosurgical instrument of claim 1, wherein the gripping parts form a pincette or forceps.

4. The electrosurgical instrument of claim 1, wherein the surface of at least one gripping part respectively facing the other gripping part is inclined or curved at least in sections such that, in a brought-together state, a gap having a width that is uneven in the longitudinal direction is formed between the gripping parts, and, when a voltage is applied to the first and the second gripping parts, the gap results in a varying electrical field strength between the first and the second gripping parts in the longitudinal direction.

5. The electrosurgical instrument of claim 4, wherein the varying electrical field strength is a linearly varying electrical field strength.

6. The electrosurgical instrument of claim 4, wherein the varying electrical field strength is a non-linearly varying electrical field strength.

7. The electrosurgical instrument of claim 4, wherein the surface of at least one gripping part respectively facing the other gripping part is configured such that the location of the strongest electrical field strength migrates in the longitudinal direction when the first limbs are moved relative to the second limbs.

8. The electrosurgical instrument of claim 1, wherein at least one of the electrically conductive sections of the at least one gripping part is movably supported in said gripping part so as to be movable relative to the gripping part.

9. The electrosurgical instrument of claim 8, wherein the conductive section with an inclined or curved surface movably supported in the respective gripping part is supported such that the conductive section with an inclined or curved surface can be moved in the gripping or counter gripping direction independently of the other conductive sections in the same gripping part.

10. The electrosurgical instrument of claim 9, wherein the movably supported section having the inclined or curved surface is accommodated in the respective gripping part such that the movably supported section performs a rolling-off movement relative to an opposite surface of the other gripping part when the instrument is moved in the gripping direction, such that during the closing movement, the point of least distance between the opposing gripping part surfaces moves in the direction toward a distal end of the instrument.

11. The electrosurgical instrument of claim 1, wherein at least one gripping part comprises three or more electrically conductive sections electrically insulated relative to each other, and the at least one gripping part comprises at least one electrically conductive section movably supported in the gripping part so as to be movable relative to its respective gripping part.

12. The electrosurgical instrument of claim 11, wherein the at least one gripping part includes guide pins for guiding the at least one movable conductive section in the gripping direction.

13. The electrosurgical instrument of claim 1, further comprising:
   a guide for laterally guiding the first and the second gripping parts, the guide acting on the instrument at least in a mostly brought-together state of the instrument.

14. The electrosurgical instrument of claim 13, wherein the guide for lateral guidance is provided on one of the plurality of insulated sections or one of the gripping parts that is divided into sections.

15. The electrosurgical instrument of claim 1, wherein the electrically conductive sections are insulated from each other by at least one insulating section, the at least one insulating section configured as a spacer extending in the gripping or counter-gripping direction and defining a minimum distance between the oppositely arranged conductive sections in a brought-together state of the instrument.

16. The electrosurgical instrument of claim 1, further comprising a rinsing channel arranged in the longitudinal direction and internal to the guide sleeve.

* * * * *